United States Patent [19]

Erbes et al.

[11] Patent Number: 5,586,155
[45] Date of Patent: Dec. 17, 1996

[54] NARROW ACCESS SCANNING POSITIONER FOR INSPECTING CORE SHROUD IN BOILING WATER REACTOR

[75] Inventors: John G. Erbes, Mt. View; Stephen B. Bayne, Fremont; John J. Ashburn, Livermore, all of Calif.

[73] Assignee: General Electric Company, San Jose, Calif.

[21] Appl. No.: 388,082

[22] Filed: Feb. 14, 1995

[51] Int. Cl.$^6$ .................................................. G21C 17/00
[52] U.S. Cl. .................. 376/249; 376/245; 376/260; 376/258; 376/252; 376/390; 376/451
[58] Field of Search .................................. 376/249, 245, 376/260, 258, 252, 390, 451; 976/DIG. 210, DIG. 213; 73/623, 625, 644

[56] References Cited

U.S. PATENT DOCUMENTS

| | | | |
|---|---|---|---|
| 3,987,666 | 10/1976 | Blanc et al. | 73/67.8 S |
| 4,165,254 | 8/1979 | Reyes | 376/249 |
| 4,548,785 | 10/1985 | Richardson et al. | 376/249 |
| 4,966,746 | 10/1990 | Richardson et al. | 376/249 |
| 5,009,105 | 4/1991 | Richardson et al. | 73/621 |
| 5,053,187 | 10/1991 | Haller | 376/258 |
| 5,068,721 | 11/1991 | Dietrich | 358/100 |
| 5,087,409 | 2/1992 | Wedellsborg et al. | 376/294 |
| 5,214,616 | 5/1993 | Terhune et al. | 367/99 |
| 5,377,237 | 12/1994 | Richardson et al. | 376/252 |
| 5,402,570 | 4/1995 | Weems et al. | 29/890.031 |

Primary Examiner—Charles T. Jordan
Assistant Examiner—Meena Chelliah
Attorney, Agent, or Firm—James E. McGinness

[57] ABSTRACT

A method and an apparatus for inspecting a core shroud by remote operation. The apparatus is a robotic scanning device which can be installed in the narrow space between the core shroud and the jet pumps and which can scan azimuthally and vertically around the circumference of the core shroud. The scanning device provides gross positioning to the area of interest and precise motion control in a limited scanning range. The scanning uses a thin wide arm to support a bank of transducers at its bottom end, and is rigidly mounted to a precision two-axis positioner at its top end. The arm is of narrow thickness to pass through the 0.5-inch access opening and to allow radial flexibility to absorb surface contour variation over the inspection area. The transducer mounting includes a water jet thruster to provide a radially inwardly directed reaction force to maintain the transducers in contact against the shroud. The arm is fabricated with a row of longitudinal holes extending throughout its length. The transducer leads are routed through some of the holes, providing them with a protective sheath for operation in the confined access. The other holes are used to conduct pressurized water from a pump to operate the jet thrusters.

20 Claims, 12 Drawing Sheets

NARROW ACCESS SCANNING POSITIONER FOR INSPECTING CORE SHROUD IN BOILING WATER REACTOR

FIELD OF THE INVENTION

This invention relates generally to nondestructive examination of material, such as metal, for voids, flaws, cracks and other defects that can be detrimental to the integrity of the material. Specifically, the invention relates to the inspection of the core shroud of a boiling water reactor.

BACKGROUND OF THE INVENTION

Figure 1A:
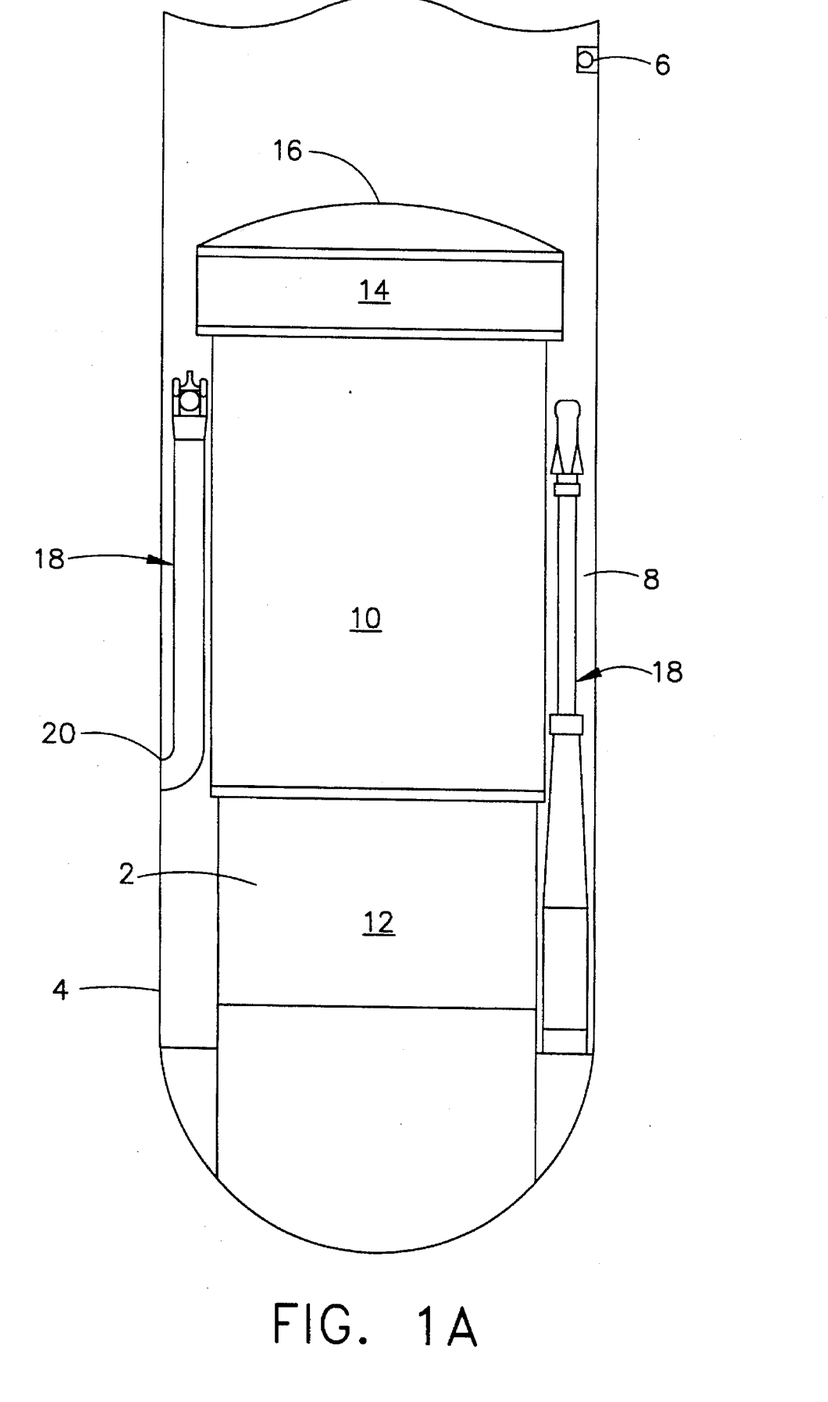
FIG. 1A is a schematic showing an elevational view of pertinent portions of a conventional BWR.

The general arrangement of a core shroud 2 inside a reactor pressure vessel (RPV) 4 is depicted in FIG. 1A. Feedwater is admitted into RPV 4 via a feedwater inlet (not shown) and a feedwater sparger 6, which is a ring-shaped pipe having suitable apertures for circumferentially distributing the feedwater inside the RPV. The feedwater from sparger 6 flows downwardly through the downcomer annulus 8, which is an annular region between core shroud 2 and RPV 4.

Core shroud 2 is a stainless steel cylinder surrounding the nuclear fuel core, the location of which is generally designated by numeral 10 in FIG. 1. The core is made up of a plurality of fuel bundle assemblies. Each array of fuel bundle assemblies is supported at the top by a top guide and at the bottom by a core plate (neither of which are shown). The core top guide provides lateral support for the top of the fuel assemblies and maintains the correct fuel channel spacing to permit control rod insertion.

The water flows through downcomer annulus 8, around the bottom edge of the shroud and into the core lower plenum 12. The water subsequently enters the fuel assemblies, wherein a boiling boundary layer is established. A mixture of water and steam enters core upper plenum 14 under the shroud head 16. The steam-water mixture then flows through vertical standpipes (not shown) atop the shroud head and enters steam separators (not shown), which separated liquid water from steam. The liquid water then mixes with feedwater in the mixing plenum, which mixture then returns to the core via the downcomer annulus. The steam is withdrawn from the RPV via a steam outlet.

The BWR also includes a coolant recirculation system which provides the forced convection flow through the core necessary to attain the required power density. A portion of the water is sucked from the lower end of the downcomer annulus 8 via recirculation water outlet (not visible in FIG. 1A) and forced by a centrifugal recirculation pump (not shown) into jet pump assemblies 18 (two of which are shown in FIG. 1A)) via recirculation water inlets 20. The BWR has two recirculation pumps, each of which provides the driving flow for a plurality of jet pump assemblies. The jet pump assemblies are circumferentially distributed around the core shroud 2.

Figure 1B:
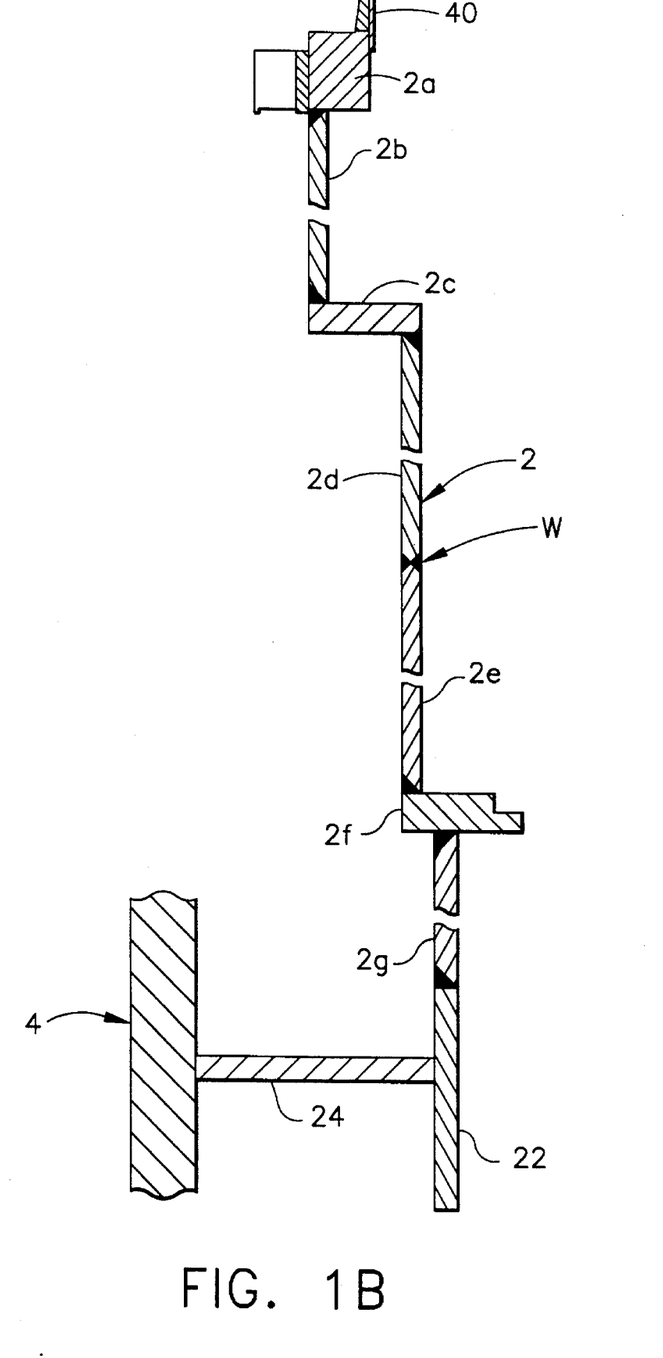
FIG. 1B is a sectional view of a portion of the core shroud incorporated in the BWR depicted in FIG. 1A.

The core shroud 2 (see FIG. 1B) comprises a shroud head flange 2a for supporting the shroud head 16; a circular cylindrical upper shroud wall 2b having a top end welded to shroud head flange 2a; an annular top guide support ring 2c welded to the bottom end of upper shroud wall 2b; a circular cylindrical middle shroud wall having a top end welded to top guide support ring 2c and consisting of upper and lower shell sections 2d and 2e joined by mid-shroud attachment weld W; and an annular core plate support ring 2f welded to the bottom end of the middle shroud wall and to the top end of a lower shroud wall 2g. (Some boiling water reactors have middle shroud wall comprising three stacked shell sections joined by attachment welds.) The entire shroud is supported by a shroud support 22, which is welded to the bottom of lower shroud wall 2g, and by annular jet pump support plate 24, which is welded at its inner diameter to shroud support 22 and at its outer diameter to RPV 4.

The material of the shroud and associated welds is austenitic stainless steel having reduced carbon content. The heat-affected zones of the shroud girth welds, including the mid-shroud attachment weld, have residual weld stresses. Therefore, the mechanisms are present for mid-shroud attachment weld W and other girth welds to be susceptible to intergranular stress corrosion cracking (IGSCC).

Stress corrosion cracking in the heat affected zone of any shroud girth seam weld diminishes the structural integrity of the shroud, which vertically and horizontally supports the core top guide and the shroud head. In particular, a cracked shroud increases the risks posed by a loss-of-coolant accident (LOCA) or seismic loads. During a LOCA, the loss of coolant from the reactor pressure vessel produces a loss of pressure above the shroud head and an increase in pressure inside the shroud, i.e., underneath the shroud head. The result is an increased lifting force on the shroud head and on the upper portions of the shroud to which the shroud head is bolted. If the core shroud has fully cracked girth welds, the lifting forces produced during a LOCA could cause the shroud to separate along the areas of cracking, producing undesirable leaking of reactor coolant. Also, if the shroud weld zones fail due to stress corrosion cracking, there is a risk of misalignment from seismic loads and damage to the core and the control rod components, which would adversely affect control rod insertion and safe shutdown.

Thus, the core shroud needs to be examined periodically to determine its structural integrity and the need for repair. Ultrasonic inspection is a known technique for detecting cracks in nuclear reactor components. The inspection area of primary interest is the outside surface of the cylindrical core shroud at the horizontal mid-shroud attachment welds. However, the core shroud is difficult to access. Installation access is limited to the annular space between the outside of the shroud and the inside of the reactor pressure vessel, between adjacent jet pumps. Scanning operation access is additionally restricted within the narrow space between the shroud and jet pumps, which is about 0.5 inch wide in some locations. The inspection areas are highly radioactive, and are located under water 50 to 65 feet below the operator's work platform. Thus, inspection of the core shroud in operational nuclear reactors requires a robotic scanning device which can be installed remotely and operated within a narrowly restricted space.

SUMMARY OF THE INVENTION

The present invention is a method and an apparatus for inspecting a core shroud. The testing apparatus is used during an outage wherein the reactor internals (i.e., steam separator and steam dryer) have been removed, which allows access to the inspection area. The testing apparatus is lowered from the refueling bridge into the reactor cavity via poles/hoists and is locked in place on the shroud flange. The apparatus is operated remotely from a central computer control station installed on the refueling floor. By use of air-actuated cylinders and motor drive mechanisms, inspection devices such as ultrasonic transducers, eddy current sensors or a closed circuit television camera can be placed in strategic positions whereat the core shroud girth welds and heat-affected zones thereof can be inspected.

More specifically, the apparatus is a robotic scanning device which can be installed in the narrow space between the core shroud and the jet pumps and which can scan azimuthally and vertically around the circumference of the core shroud. The scanning device provides gross positioning to the area of interest and precise motion control in a limited scanning range.

The scanning device in accordance with the preferred embodiment of the invention uses a thin wide arm to support a bank of transducers at its bottom end, and is rigidly mounted to a precision two-axis positioner at its top end. The overall design allows projection of a precise scanning motion from the upper end where there is space for the positioner mechanism, through the narrow access opening, to the transducers at the inspection area. By its geometry, the transducer arm is stiff in the plane of the scanning motion to accurately transmit this motion to the transducers. It is, however, of narrow thickness to pass through the 0.5-inch access opening and to allow radial flexibility to absorb surface contour variation over the inspection area. The transducer mounting includes one or more water jet thrusters to provide a radially inwardly directed reaction force to maintain the transducers in contact against the shroud. The arm is fabricated with a row of longitudinal holes extending throughout its length. The transducer leads are routed through some of the holes, providing them with a protective sheath for operation in the confined access. The other holes are used to conduct pressurized water from a pump to operate the jet thrusters.

The two-axis positioner consists of two slide rails oriented at 90° relative to each other, with ball bearing carriages. The horizontal slide is mounted to the clamping fixture. The vertical slide is mounted to the carriage of the horizontal slide, allowing the vertical slide carriage to move in both directions. Motion in each direction is controlled by a respective servo motor with resolver position feedback. Horizontal axis motion is transmitted from the motor to the carriage by a direct belt and pulley drive. Vertical motion is transmitted from the motor to the carriage through a ball screw and nut drive. Each servo motor is operated by a computer-controlled power supply, through which the desired scanning motion is specified.

The clamping fixture design takes advantage of the existing upper shroud geometry, using it as a third rail for gross circumferential positioning around the shroud periphery. During gross positioning, the scanner assembly weight is supported on the shroud steam dam by the clamping fixture tractor drive wheel. The tractor drive wheel is powered by a third servo motor, allowing gross position control. Guide rollers facilitate smooth motion of the fixture around the shroud circumference. The shroud flange has shroud head bolt lugs spaced around its periphery, which are used to define repeatable index positions for correlating inspection data. In circumferential positioning, a pneumatic cylinder is utilized which, when extended, contacts the next lug to provide a positive position stop. Retracting the piston then allows travel past a lug to the next location. When the desired position is reached, one or more pneumatic clamp cylinders are operated so that their respective piston rods extend down against the top of the shroud flange, thereby clamping the fixture rigidly in place. The two-axis positioner is thus provided with a series of repeatable fixed operating positions around the shroud circumference, utilizing existing features of the shroud design.

DETAILED DESCRIPTION OF THE PREFERRED EMBODIMENTS

Figure 2:
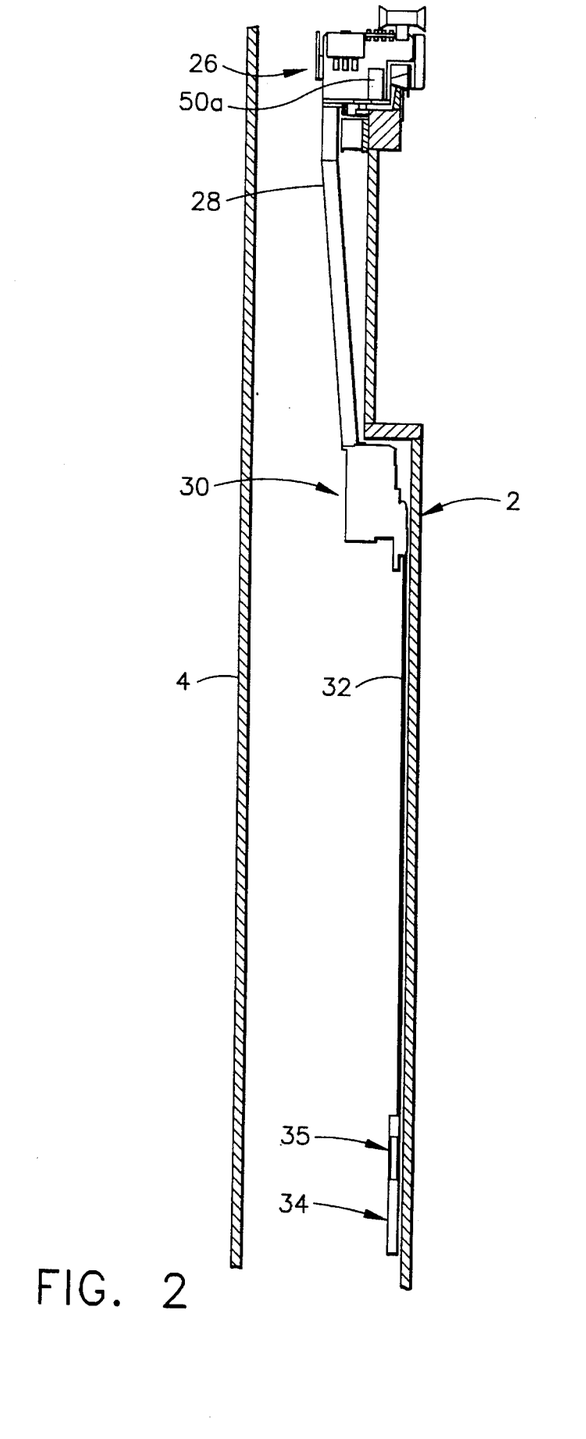
FIG. 2 is an elevation view of a scanner positioning tool in accordance with the preferred embodiment of the invention, shown installed on the core shroud.

As shown in FIG. 2, the narrow access scanner positioning tool in accordance with the preferred embodiment of the invention is installed onto the top of the core shroud and extends downward to the girth weld being inspected. For the purpose of this discussion, a tool designed for inspecting a mid-shroud attachment weld W will be described in detail. The small profile of the tool makes it possible to maneuver between the shroud outer diameter and the jet pumps (not shown in FIG. 2). This decreases the time needed to perform the full inspection around the shroud circumference.

The inspection tooling comprises a gross positioning assembly 26 which is supported by and travels along the lip of the shroud. When the desired position is reached, the tool is clamped to prevent further movement. A rigid spine 28 is connected to and extends vertically downward from the assembly 26. Spine 28 supports a two-axis positioner 30, which is located at an elevation below the top guide support ring 2c. A resilient scan arm 32, having a reduced thickness allowing the scan arm to pass between the shroud outer diameter and a jet pump, is connected to and extends vertically downward from the two-axis positioner 30. The two-axis positioner can be actuated to displace the scan arm vertically or circumferentially along the outside of the shroud.

The bottom end of scan arm 32 supports a transducer sled 34 which carries a plurality of ultrasonic transducers. Transducer sled 34 is pressed against the shroud outer diameter by a water jet thruster 35 or other thrust device (e.g., a motorized propeller), thereby ensuring continued contact between the transducers and the weld surface. The transducers are used to inspect the mid-shroud attachment weld(s). The scan arm 32 is preferably made from control blade material stock, which consists of a multiplicity of parallel square tubes electron beam welded together in a linear side-by-side array. The array of parallel channels inside the control blade material provide conduits for coaxial cables connecting the ultrasonic transducers to the signal processing station and for hydraulic lines which supply pressurized water to the water jet thruster.

Figure 3A:
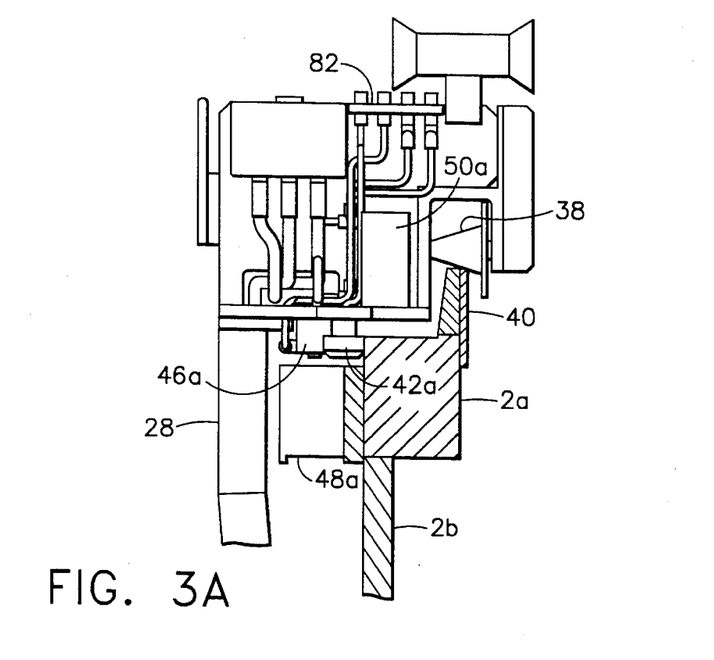
FIGS. 3A and 3B are elevation views of the upper and middle assemblies, respectively, of the scanner positioning tool in accordance with the preferred embodiment, shown in relationship to corresponding portions of the core shroud.
Figure 4A:
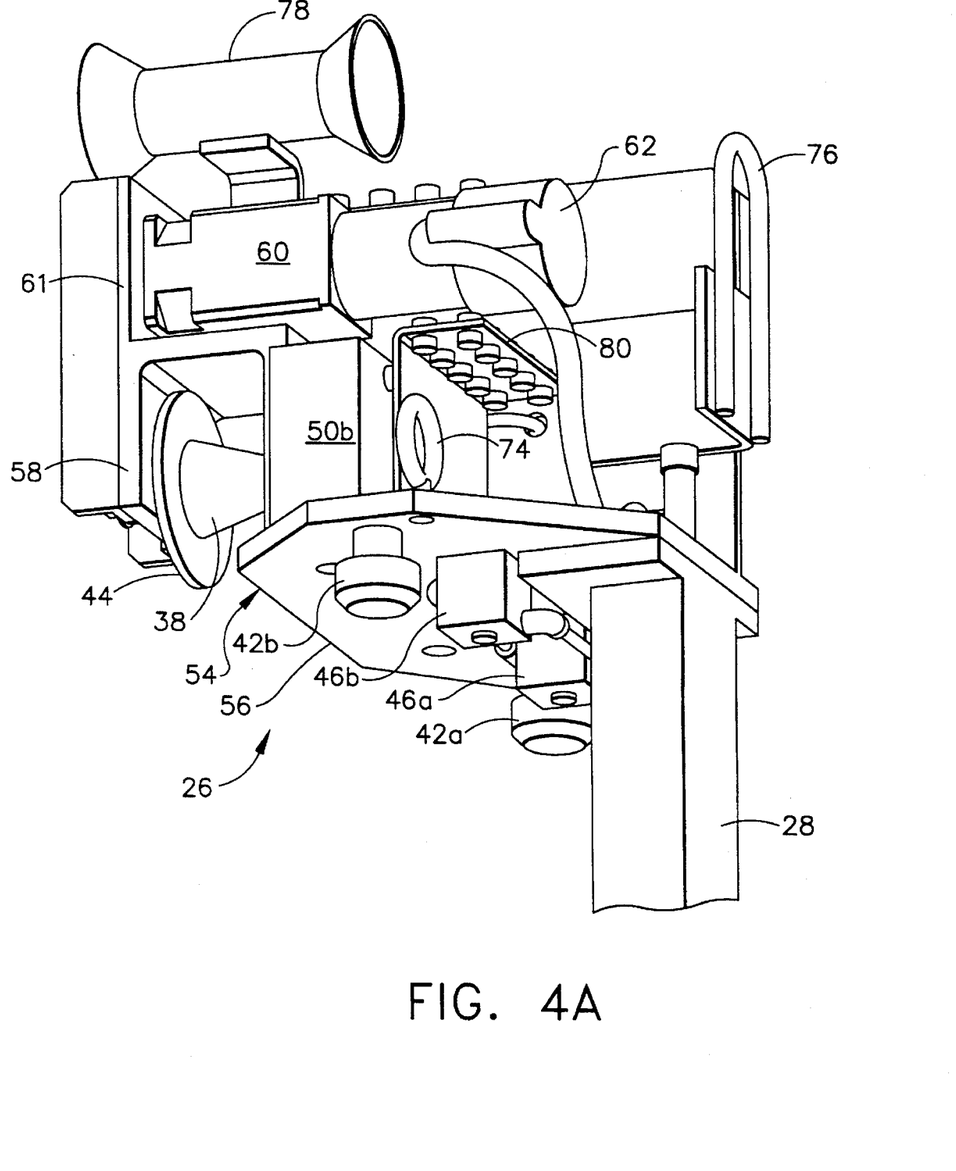
FIGS. 4A and 4B are isometric views of the upper assembly of the scanner positioning tool in accordance with the preferred embodiment, taken from different vantage points.

Referring to FIGS. 3A and 4A, the gross positioning assem-bly comprises a servo motor 62 and gear reduction 60 for driving a conical tractor drive wheel 38 which rides on steam dam 40. The tractor drive wheel 38, when loaded with the weight of the tool, can move the tool along the shroud lip to a position desired by the operator. A pair of cam rollers 42a and 42b (see FIG. 4B), located beneath the drive assembly, contact the outer diameter of the shroud and provide stability during motion. A drive wheel stop 44 prevents drive wheel 38 from falling off the steam dam.

Figure 3B:
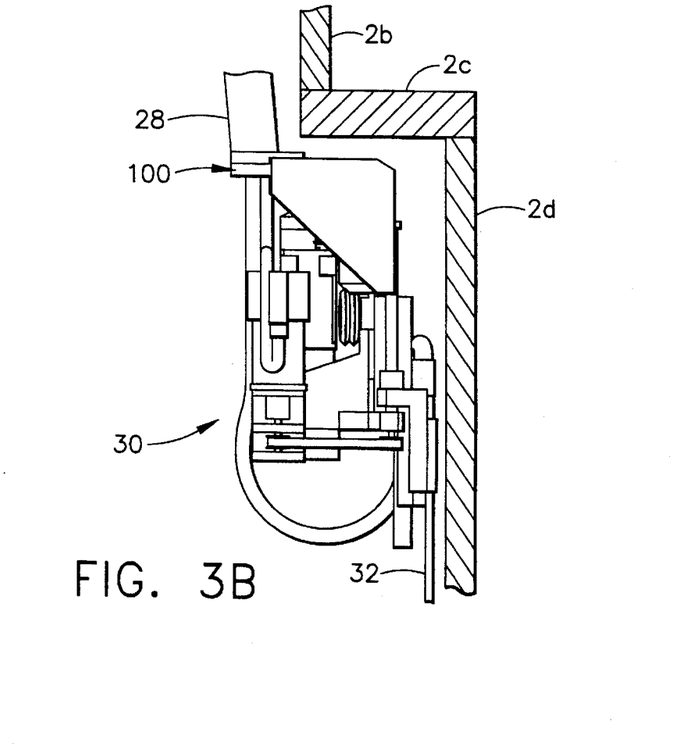
Figure 4B:
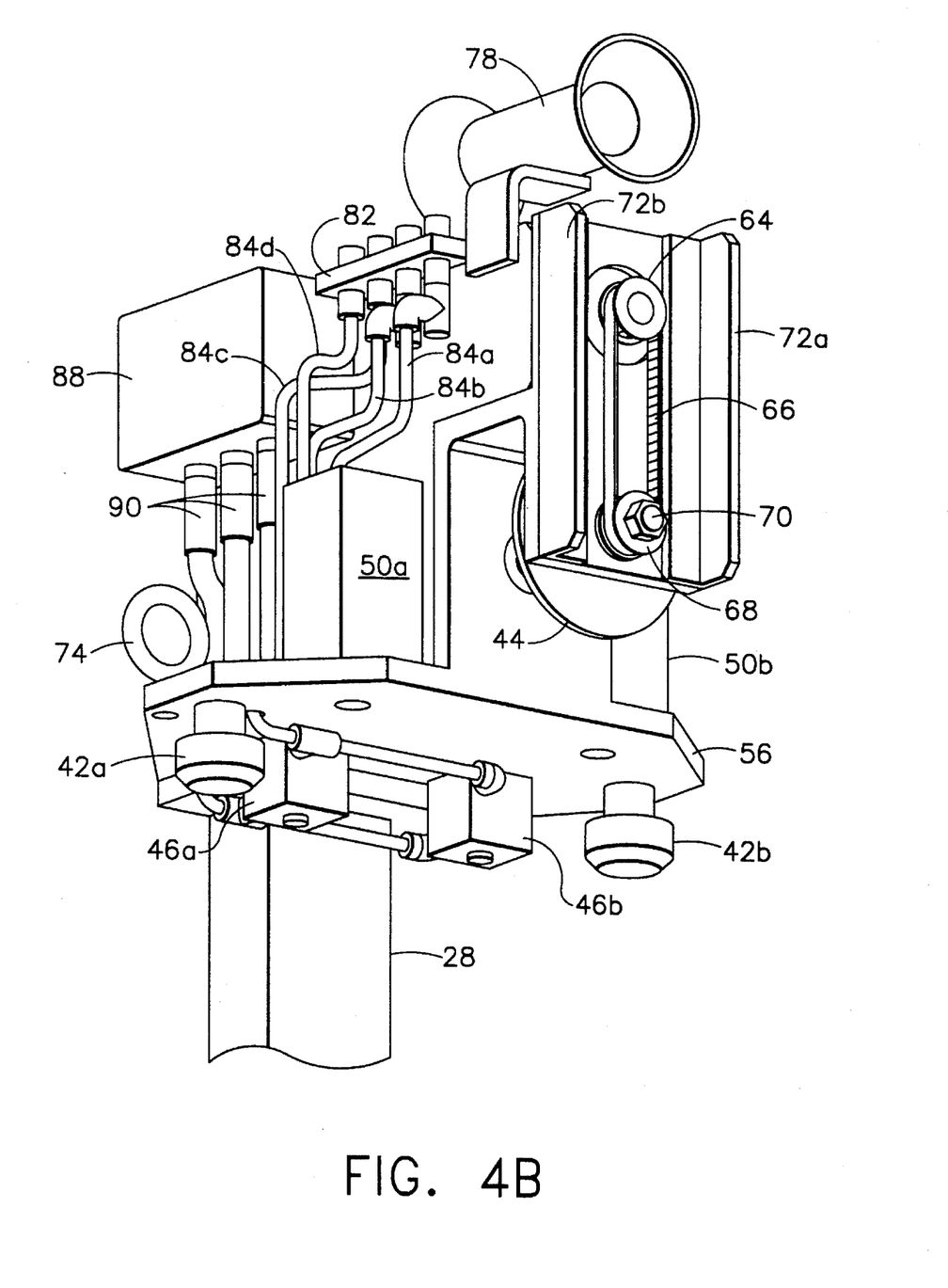
Figure 5A:
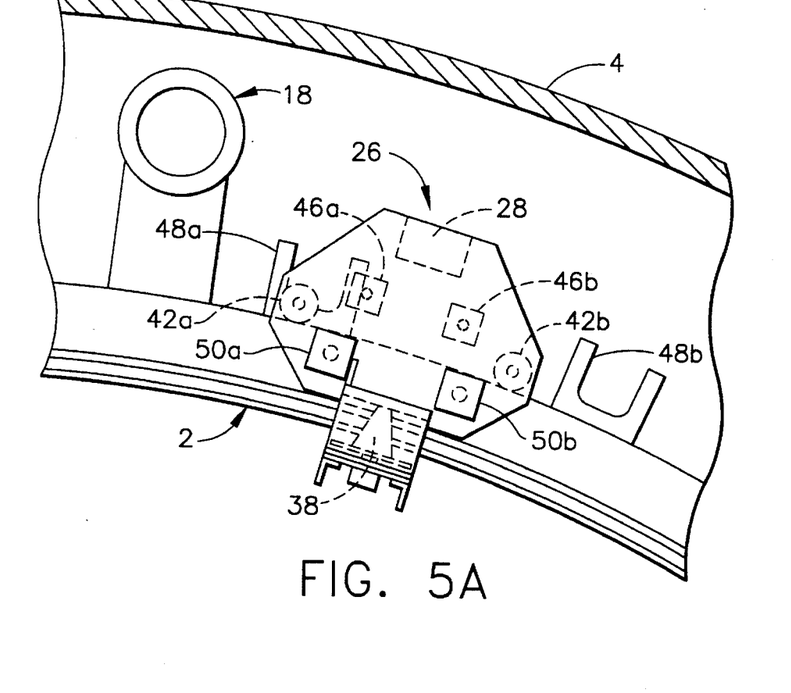
FIGS. 5A and 5B are plan views showing two indexing positions resulting from circumferential travel of the upper assembly between adjacent shroud head bolt lugs.

The gross positioning assembly 26 also comprises a pair of air-actuated positioning cylinders 46a and 46b (see FIG. 4B). After the two-axis positioner 30 (FIG. 2) is properly seated below the top guide support ring 2c, the cam rollers 42a and 42b are in contact with the shroud and the drive wheel 38 is properly seated on the steam dam, the tool is driven to an azimuthal position whereat the piston rods of positioning cylinders 46a and 46b overlie positions between two adjacent shroud lugs 48a and 48b. The piston rods of positioning cylinders 46a and 46b are extended and then the tool is driven counterclockwise towards shroud lug 48a until the piston rod of positioning cylinder 46a contacts the shroud lug 48a (see FIG. 5A). At this stage the piston rods of a pair of air-actuated clamping cylinders 50a and 50b are extended into engagement with the top surface of shroud flange 2a and then the piston rods of positioning cylinders 46a and 46b are retracted. The clamping cylinders 50a and 50b lift the tool, thereby lifting the tractor drive wheel 38 slightly from the steam dam 40. The tool is lifted until the bottom plate 100 (see FIG. 3B) of the middle assembly supporting the two-axis positioner 30 contacts the underside of the top guide support plate 2c. This causes the tool to effectively "clamp" itself to the top portion of the shroud and remain motionless while an inspection is performed. The water jet 35 (see FIG. 2) is then turned on to full thrust to allow the transducer package 34 to contact the shroud wall. Then a predetermined scanning sequence is performed in which the transducer package is scanned vertically and circumferentially over the weld surface by remote computer control of the two-axis positioner, through the two servo motors.

Figure 5B:
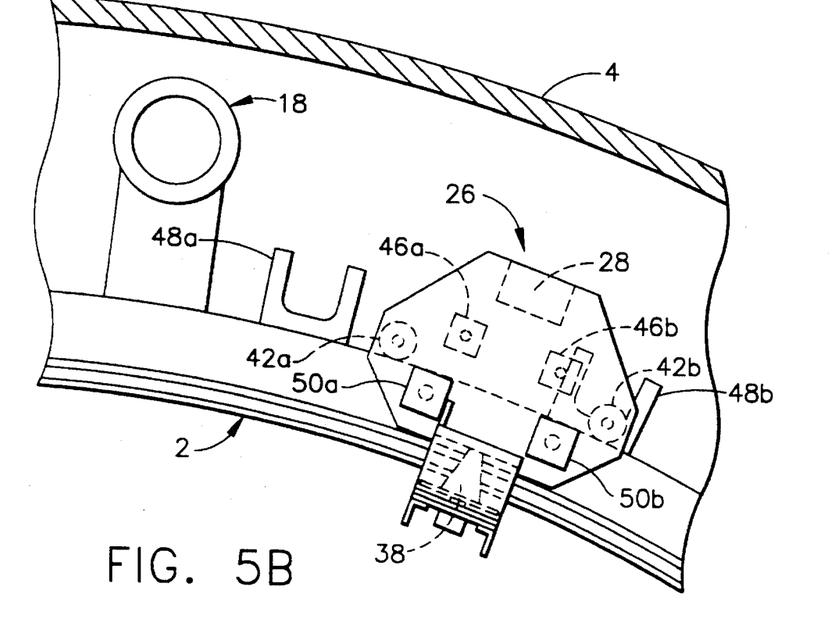

Once the scanning sequence is completed, the water jet is turned off and the piston rods of the clamping cylinders 50a and 50b are retracted. Retraction of the piston rods of the clamping cylinders 50a and 50b enables the tool to lower, resting the tractor drive wheel 38 on the steam dam 40. The tool is then driven to the next desired azimuthal position whereat the piston rod of positioning cylinder 46a or 46b again overlies a position adjacent to shroud lug 48a or 48b. The piston rod of positioning cylinder 46b is again extended and then the tool is driven clockwise towards shroud lug 48b until the piston rod of positioning cylinder 46b contacts shroud lug 48b (see FIG. 5B). This indexing may be performed in the counterclockwise direction instead, and may use cylinder 46a as a locating stop instead. Combined with the available choices in selection of shroud lugs, optimum indexing strategy may be specified for complete and repeatable scan coverage of any given shroud. As before, the piston rods of air-actuated clamping cylinders 50a and 50b are extended and the piston rods of positioning cylinders 46a and 46b are retracted to lock the tool in position for the next cycle of the predetermined scanning sequence.

The structural details of the gross positioning assembly 26 are depicted in FIGS. 4A and 4B. A welded positioner block assembly 54 supports all of the operating components of assembly 26. As seen in FIG. 4A, the base plate 56 supports the air-actuated cylinders 46a, 46b, 50a and 50b. The positioning cylinders 46a and 46b are mounted on the bottom surface of base plate 56 with their piston rods extendible away from the plate, whereas the clamping cylinders 50a and 50b are mounted on the top surface of base plate 56 with their piston rods extendible through respective holes in the base plate 56. Likewise the cam rollers 42a and 42b are pivotably mounted on the base plate 56. Base plate 56 supports the remaining structure of positioner block assembly 54 as well as the spine 28. An inverted U-shaped mounting plate 58 has a pair of legs which pivotably support the tractor drive wheel 38. The end of one leg is joined to base plate 54; the other leg extends upward to form a motor mounting plate 61 which supports gearhead 60 and motor 62 for driving rotation of tractor drive wheel 38. Motor 62 is coupled to tractor drive wheel 38 in conventional fashion via drive pulley 64, timing belt 66, drive shaft pulley 68 and drive shaft 70, as seen in FIG. 4B. Damage to the pulleys is prevented by pulley guards 72a and 72b.

Referring to FIG. 4A, the positioner block assembly 54 also supports various structures, such as eye hooks 74, lifting eye 76 and tube 78, for lifting and manipulating the inspection tool using service pools, grapples and similar conventional devices.

Figure 10:
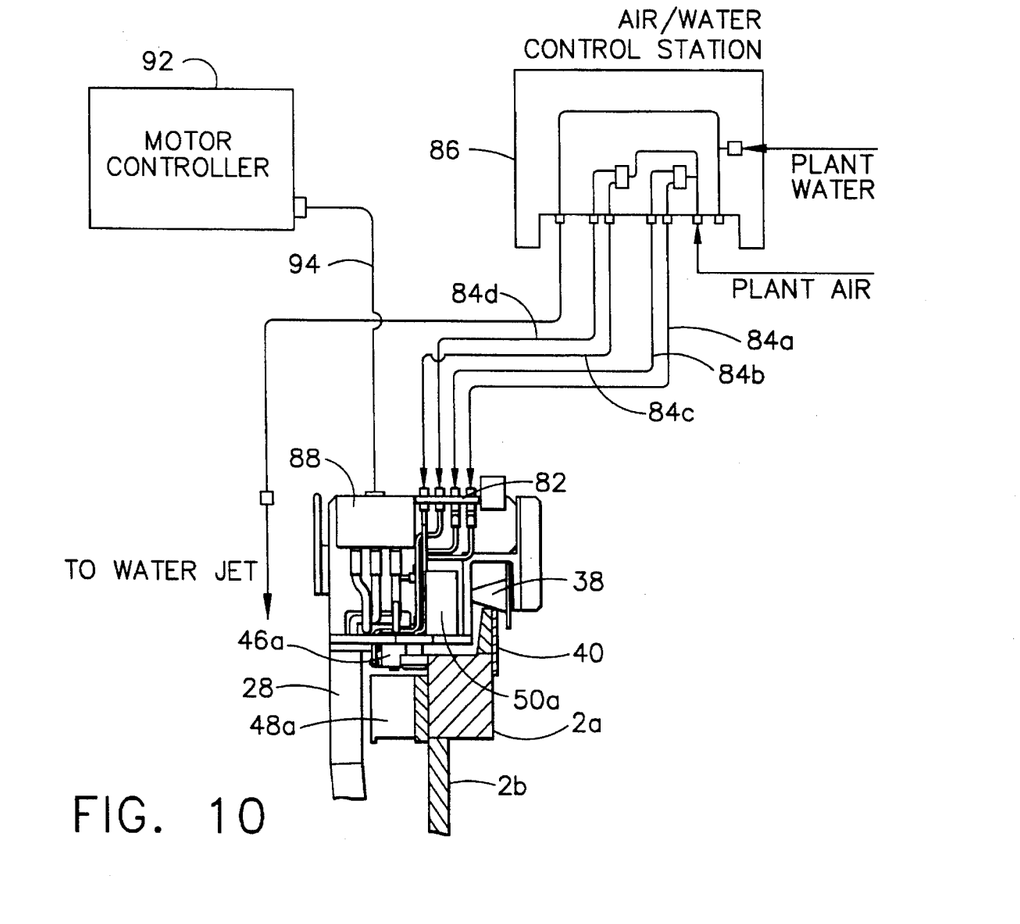
FIG. 10 is a schematic showing the electrical, pneumatic and hydraulic connections to the scanner positioning tool in accordance with the preferred embodiment.

As seen in FIG. 4A, the positioner block assembly comprises a plate 80 for supporting the coaxial cables 5 (not shown) which control the ultrasonic transducers. Referring to FIGS. 4B and 10, positioner block assembly 54 further comprises a block 82 for supporting the lines 84a-d which supply pressurized air from an air/water control station 86 to the air-actuated cylinders, and a box 88 containing the junctions for connecting the motor cables 90 to the motor controller 92 via a motor umbilical cable 94. Line 84a extends the clamping cylinders; line 84b retracts the clamping cylinders; line 84c extends the positioning cylinders; and line 84d retracts the positioning cylinders.

Figure 6:
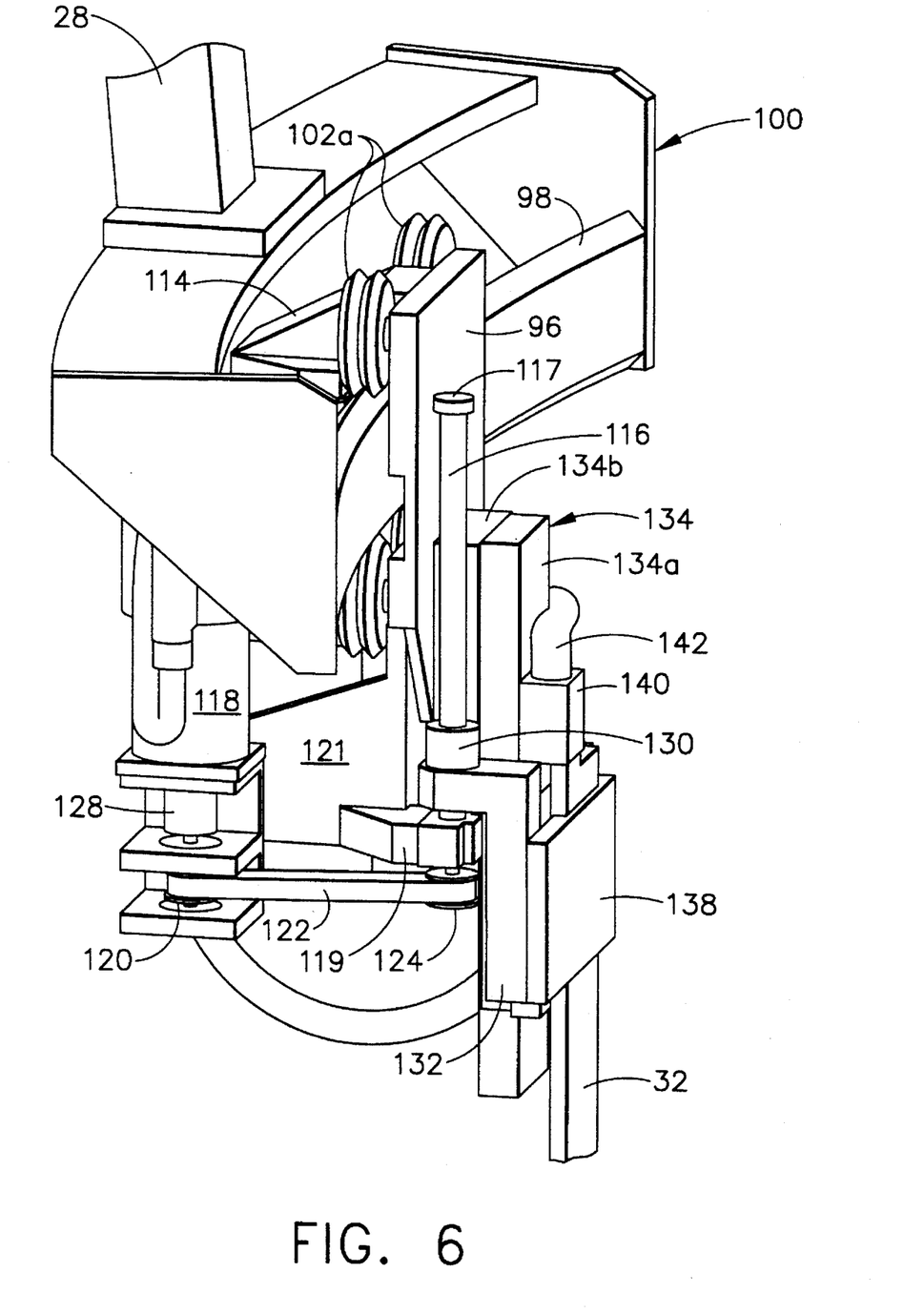
FIG. 6 is an isometric view of the middle assembly of the scanner positioning tool in accordance with the preferred embodiment.

The movement of the ultrasonic transducer package relative to the gross positioning assembly is controlled by the two-axis positioner 30, which rests just under the lip of the shroud (i.e., the top guide support ring 2c). Referring to FIG. 6, the two-axis positioner 30 comprises a carriage 96 which rides on a horizontal curved track 98. The curved track is supported at opposite ends by a support frame assembly 100 which is rigidly connected to the bottom end of spine 28. The carriage 96 has an upper pair of guide rollers 102a which roll on an upper guide surface 98a of curved track 98 and a lower pair of guide rollers 102b which roll on a lower guide surface 98b of curved track 98. In accordance with the preferred embodiment, the guide rollers have V-shaped grooves about their circumference which form-fit with guide surfaces 98a and 98b having a V-shaped cross section. Movement of carriage 96 along track 98 causes the transducer package 34 (see FIG. 2) to scan horizontally. Preferably the curvature of the track 98 corresponds to a radius from the center of the shroud.

Figure 7A:
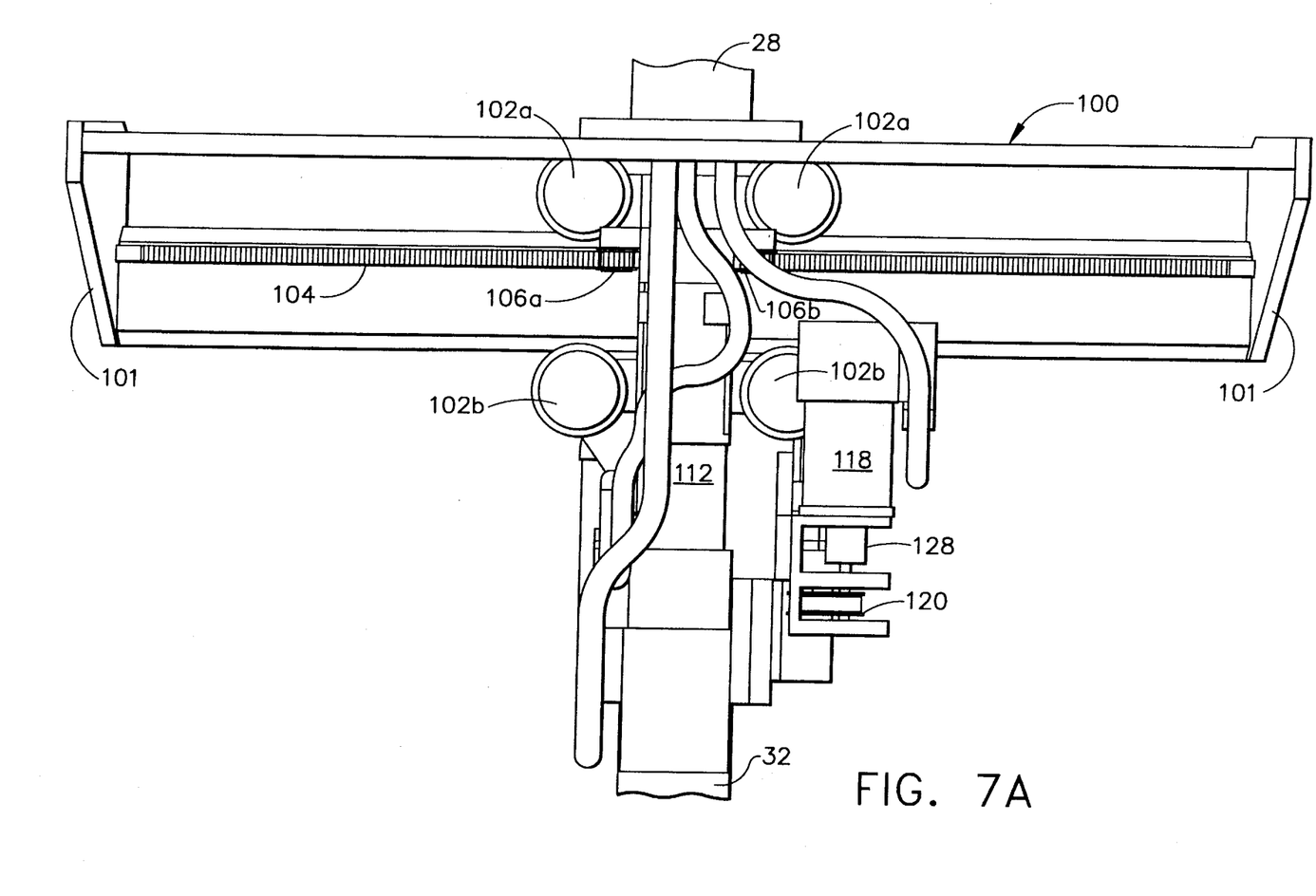
FIGS. 7A and 7B are front elevation and plan views, respectively, of the horizontal scan drive incorporated in the middle assembly shown in FIG. 6.
Figure 7B:
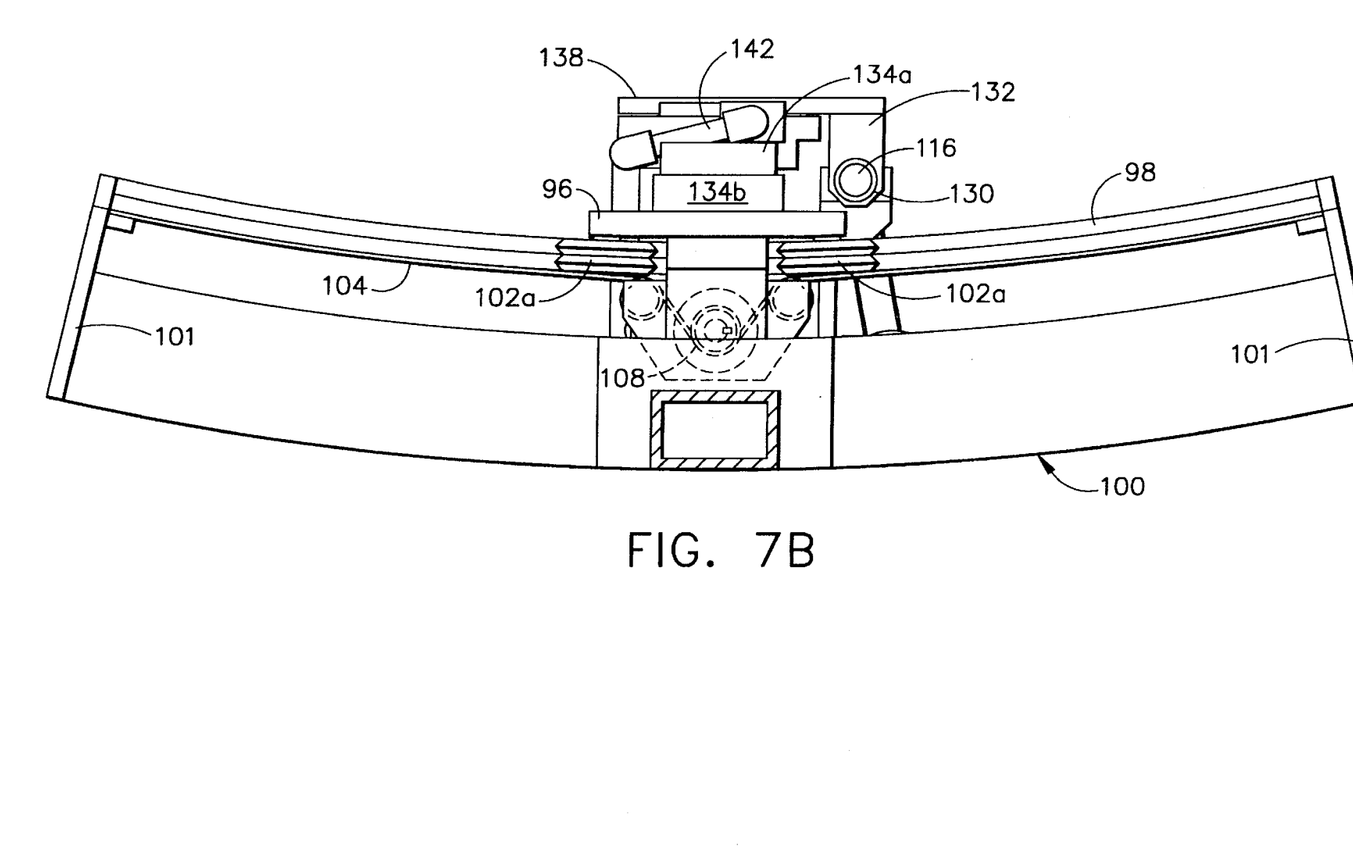

The horizontal drive scan is shown in FIGS. 7A and 7B. A flexible toothed belt 104 has its ends anchored to opposing ends 101 of support frame assembly 100. The toothed belt 104 is threaded between a pair of idler pulleys 106a and 106b and a drive shaft pulley 108, as best seen in FIG. 7B. The pulleys 106a, 106b and 108 have means for intermeshing with the teeth of belt 104. Drive shaft pulley 108 is mounted on the end of a drive shaft 110 of a drive motor 112 which is attached to the carriage 96 by a motor mount 114 (see FIG. 6). In response to actuation of drive motor 112, the drive shaft pulley 108 is rotated. During this rotation, pulley 108 travels along the toothed belt, causing carriage 96 to roll along the curved track.

Referring again to FIG. 6, the vertical scan drive comprises a lead screw 116, rotatably supported by thrust bearings in a pillow block 119. The lead screw is driven to rotate by a drive motor 118 via a drive motor pulley 120, a timing belt 122 and a drive shaft pulley 124 in conventional fashion. The pulley shaft 126 is coupled to the motor drive shaft via a flexible coupling 128 which minimizes shaft misalignment loads. The drive motor 118 is supported by a motor bracket 121 connected to carriage 96. Therefore, drive motor 118 travels horizontally in conjunction with carriage 96.

The lead screw 116 is threadably coupled to a ball nut 130 connected to a ball nut bracket 132. Ball nut bracket 132 is in turn connected to the sliding part 134a of a linear bearing 134. The sliding part 134a of linear bearing 134 also carries the scan arm mounting block 138, which supports the scan arm 32. In response to rotation of lead screw 116, the ball nut 130 and parts connected thereto, including scan arm 32, are displaced up or down depending on the direction of lead screw rotation. The stop 117 prevents the ball nut 130 from unscrewing off the end of lead screw 116.

The scan arm 32 is made from control blade material having a plurality of parallel channels which carry pressurized water to the water jet thruster. A header assembly 140 has an input connected to tubing 142 and a plurality of outputs connected to respective channels in the scan arm. Thus, the pressurized water from the air/water control station is separated into a plurality of streams which flow from one end of the scan arm to the other end.

The entire assembly comprising scan arm 32, scan arm mounting plate 138, header assembly 140, ball nut bracket 132, ball nut 130 and sliding part 134a of linear bearing 134 is vertically slidable relative to the stationary part 134b of linear bearing 134, which is connected to horizontally slidable carriage 96. As a result, the scan arm 32, and consequently the transducer package 34 mounted on the lower end thereof, can be scanned vertically and circumferentially relative to the outer circumference of the core shroud by remote operation of drive motors 112 and 118.

Figure 8:
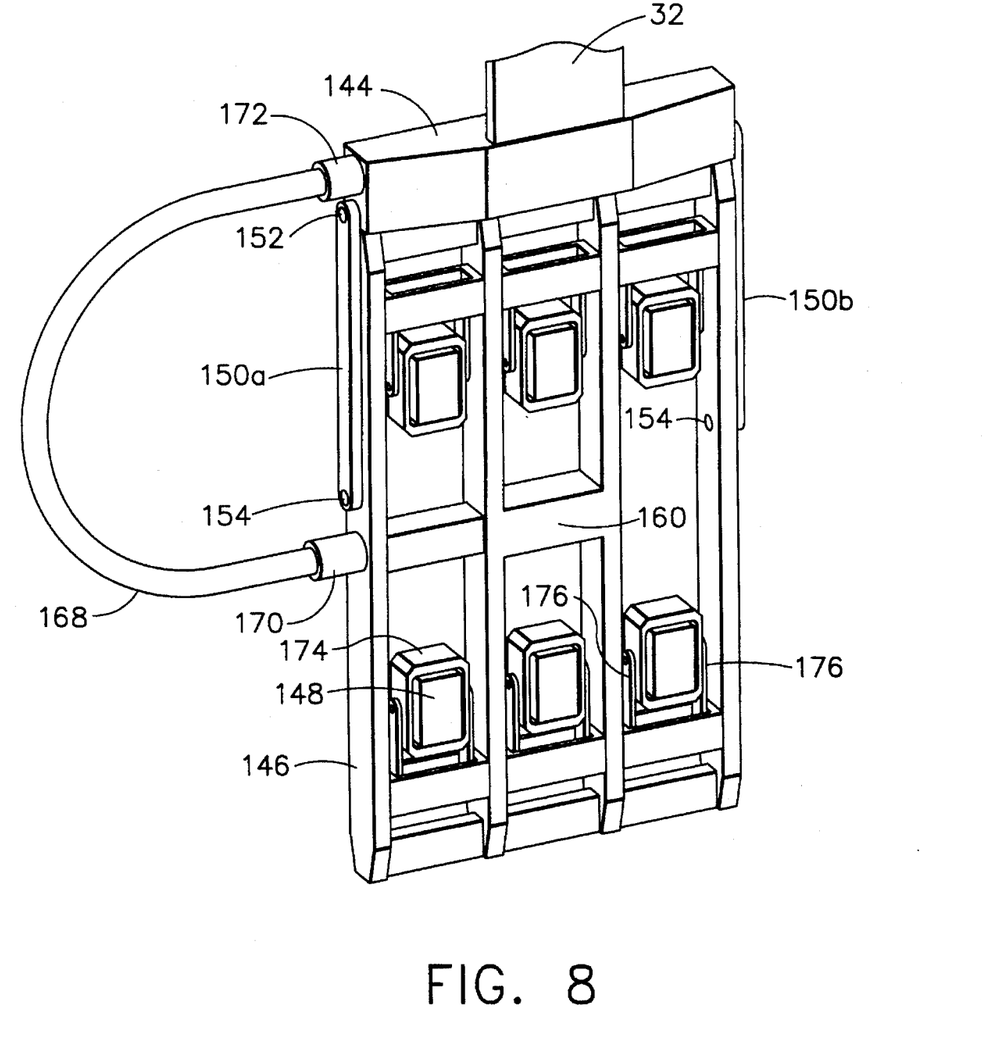
FIG. 8 is an isometric view of the lower assembly of the scanner positioning tool in accordance with the preferred embodiment.

As shown in FIG. 8, the transducer package 34 is pivotably mounted on a base 144 connected to the lower end of the scan arm 32. The transducer package comprises a sled 146 which carries an array of ultrasonic transducers 148. Sled 146 is pivotably suspended from base 144 via a pair of linkages 150a and 150b. The linkages are pivotably coupled to the base 144 via a pair of coaxial pivot pins 152. The sled 146 is pivotably coupled to the linkages by a pair of coaxial pivot pins 154. The axis of pivot pins 152 is parallel to the axis of pivot pins 154. Thus, sled 146 is able to swing about the axis of pivot pins 152 and rotate about the axis of pivot pins 154.

Figure 9:
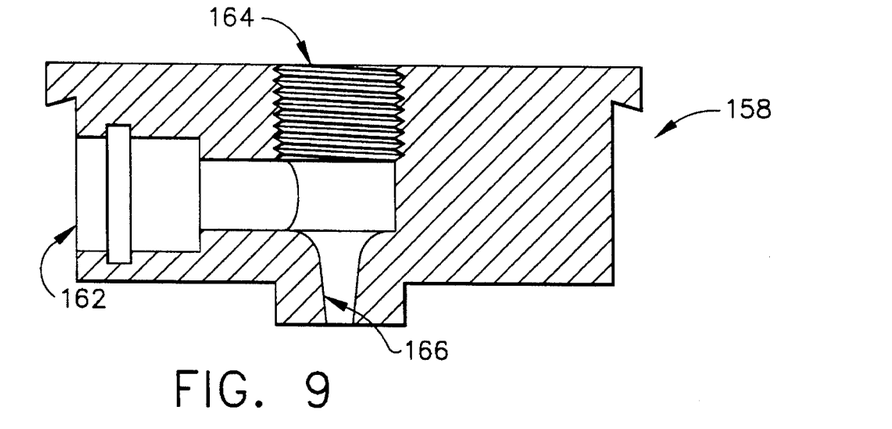
FIG. 9 is a sectional view of the water jet thruster nozzle incorporated in the lower assembly shown in FIG. 8.

The sled 146 is thrust against the outer circumferential surface of the shroud by a water jet thruster 35 which comprises a jet box 158 (see FIG. 9) attached to a jet plate 160 (see FIG. 8). The jet box 158 comprises an inlet 162, an opening 164 for receiving a plug (not shown) and a water jet thruster nozzle 166. The jet box is made of aluminum. The inlet 162 is in flow communication with tubing 168 (see FIG. 8) via a connector 170. The other end of tubing 168 is in flow communication with the outlet of a manifold passage incorporated in the base 144 via a connector 172. The manifold has a plurality of inputs connected to the plurality of parallel channels which carry pressurized water along the length of the scan arm. The plurality of manifold inputs all feed into the single manifold output, whereby the separate streams of pressurized water are combined. As a result, the pressurized water from the air/water control station flows at high speed out of the nozzle 166 (see FIG. 9). The thrust produced by this water jet presses the sled 146 against the outer shroud surface.

Each of the ultrasonic transducers 148 is mounted in a respective holder 174. Each holder 174 is attached to the sled 146 by a pair of forked arms 176. Each transducer mounting can be one of two types. In the first type, the transducer is rotatable about a vertical axis within the holder and the holder is rotatable about a horizontal axis relative to the forked arms, which are fixed to the sled. In the second type, the transducer is fixed in the holder, the fixed arms are mounted on axles and independently rotatable relative to the sled, and the holder is pivotably coupled on one side to one forked arm and on the other side to the other forked arm. Torsion springs (not shown) are hooked onto the forks to resist rotation of the forked arms away from their equilibrium positions. Both types of transducer mountings function as spring-loaded gimbals which allow each transducer to be independently oriented to conform to the contour of the shroud and weld crown surfaces.

Each ultrasonic transducer has two cables (not shown). These cables are distributed in four channels in the scan arm. Four other channels in the scan arm are used for the water lines.

The foregoing preferred embodiment has been disclosed for the purpose of illustration. Variations and modifications which do not depart from the broad concept of the invention will be readily apparent to those skilled in the design of ultrasonic inspection equipment. For example, it will be apparent that the gross positioning assembly may incorporate two tractor drive wheels instead of one. All such variations and modifications are intended to be encompassed by the claims set forth hereinafter.

We claim:

1. An apparatus for remotely inspecting a girth weld in a core shroud, comprising:

a clamping fixture which clamps onto the shroud;

a curved track connected to said clamping fixture;

a two-axis positioner comprising a carriage, means for moving said carriage along said curved track, a mounting, and means for vertically displacing said mounting relative to said carriage;

an extension arm having a top end connected to said mounting; and an inspection device mounted on a bottom end of said extension arm, wherein said extension arm has a length such that said inspection device is located at an elevation near the elevation of said girth weld, is flexible in a radial direction and is stiff in a plane of scanning motion perpendicular to said radial direction, and said inspection device can be scanned vertically and azimuthally in said plane of scanning motion by operation of said two-axis positioner.

2. The apparatus as defined in claim 1, wherein said inspection device comprises an ultrasonic transducer.

3. The apparatus as defined in claim 2, further comprising means for allowing said ultrasonic transducer to self-orient to conform to the contour of the opposing area of the shroud surface.

4. The apparatus as defined in claim 1, further comprising means for thrusting said inspection device radially inward into contact with the opposing area of the shroud surface.

5. The apparatus as defined in claim 4, wherein said thrusting means comprises a water jet nozzle, and said extension arm comprises a plurality of parallel tubes welded together in a linear side-by-side array, each of said parallel tubes having a channel, at least one of said channels having one end in flow communication with a source of pressurized water and the other end in flow communication with said water jet nozzle.

6. The apparatus as defined in claim 1, wherein said extension arm is made of control blade material.

7. The apparatus as defined in claim 1, wherein said means for moving said carriage along said curved track comprises a toothed pulley driven by a motor which travels with said carriage, and a toothed belt having its ends fixed relative to said curved track, said toothed pulley engaging said toothed belt.

8. The apparatus as defined in claim 1, wherein said means for vertically displacing said mounting relative to said carriage along said curved track comprises a linear bearing having a stationary part carried by said carriage and a moving part which slides relative to said stationary part, a lead screw driven by a motor carried by said carriage, and a ball nut threadably engaging said lead screw and carried by said moving part of said linear bearing.

9. The apparatus as defined in claim 1, further comprising a tractor drive wheel rotatably mounted on said clamping fixture and a motor for driving said tractor drive wheel, wherein said clamping fixture comprises a first air-actuated cylinder having a piston rod which is extended in a first operational state to lift said tractor drive wheel relative to the shroud and which is retracted in a second operational state to lower said tractor drive wheel relative to the shroud, whereby said tractor drive wheel disengages from the shroud and said clamping fixture clamps onto the shroud in said first operational state, and said tractor drive wheel engages the shroud and said clamping fixture unclamps from the shroud in said second operational state, said tractor drive wheel causing said apparatus to travel along the circumference of the shroud when said motor is actuated in said second operational state.

10. The apparatus as defined in claim 9, further comprising a second air-actuated cylinder having a piston rod which can be extended to interfere with a shroud head bolt lug during travel of said apparatus along the circumference of the shroud in said second operational state.

11. An inspection apparatus comprising:
 a conical tractor drive wheel;
 means for pivotably supporting said tractor drive wheel;
 a motor for driving said tractor drive wheel to rotate;
 a support structure having a top end connected to said means for pivotably supporting said tractor drive wheel and having a bottom end;
 an inspection device mounted on said bottom end of said support structure.

12. The apparatus as defined in claim 11, further comprising means for thrusting said support structure in a predetermined direction.

13. The apparatus as defined in claim 12, wherein said thrusting means comprises a water jet nozzle, and said extension arm comprises a plurality of parallel tubes welded together in a linear side-by-side array, each of said parallel tubes having a channel, at least one of said channels having one end in flow communication with a source of pressurized water and the other end in flow communication with said water jet nozzle.

14. The apparatus as defined in claim 11, further comprising a clamping fixture for attaching said apparatus to the shroud of a nuclear reactor.

15. The apparatus as defined in claim 11, further comprising means for indexing the azimuthal position of the tractor drive wheel relative to a shroud head bolt lug.

16. A method for inspecting a girth weld in a core shroud of a nuclear reactor, comprising the steps of:
 suspending an inspection tool assembly from the upper rim of the core shroud at a first predetermined gross azimuthal position such that an inspection device incorporated in said inspection tool assembly is located at a predetermined gross elevation relative to a girth weld to be inspected and such that an extension arm incorporated in said inspection tool assembly for supporting said inspection device extends into a space between a jet pump assembly and the core shroud; and
 scanning said inspection device azimuthally and vertically relative to said inspection tool assembly while said inspection tool assembly is located at said first predetermined gross azimuthal position.

17. The method as defined in claim 16, further comprising the steps of:
 moving said inspection tool assembly along the upper rim of the core shroud from said first predetermined gross azimuthal position to a second predetermined gross azimuthal position; and
 scanning said inspection device azimuthally and vertically relative to said inspection tool assembly while said inspection tool assembly is located at said second predetermined gross azimuthal position.

18. The method as defined in claim 17, further comprising the step of indexing said first predetermined gross azimuthal position relative to a shroud head bolt lug.

19. The method as defined in claim 17, further comprising the step of maintaining said inspection device in contact with the outer circumferential surface of the core shroud by thrusting water in a radially outward direction away from the inspection device.

20. An apparatus for remotely inspecting a girth weld in a core shroud, comprising:
 a clamping fixture which clamps onto the shroud;
 a two-axis positioner supported by said clamping fixture and comprising a mounting which is movable vertically and azimuthally relative to the shroud;
 an extension arm having a top end connected to said mounting; and
 an inspection device mounted on a bottom end of said extension arm,
 wherein said extension arm has a length such that said inspection device is located at an elevation near the elevation of said girth weld, is flexible in a radial direction and is stiff in a plane of scanning motion perpendicular to said radial direction, and said inspection device can be scanned vertically and azimuthally in said plane of scanning motion by operation of said two-axis positioner.

* * * * *